(12) United States Patent
Abenaim et al.

(10) Patent No.: US 9,044,152 B2
(45) Date of Patent: Jun. 2, 2015

(54) ROTATABLE DRUM ASSEMBLY FOR RADIOLOGY IMAGING MODALITIES

(75) Inventors: Daniel Abenaim, Lynnfield, MA (US);
Ronald E. Swain, Reading, MA (US)

(73) Assignee: Analogic Corporation, Peabody, MA (US)

( * ) Notice: Subject to any disclaimer, the term of this patent is extended or adjusted under 35 U.S.C. 154(b) by 336 days.

(21) Appl. No.: 13/440,432

(22) Filed: Apr. 5, 2012

(65) Prior Publication Data

US 2013/0266116 A1 Oct. 10, 2013

(51) Int. Cl.
*A61B 6/03* (2006.01)

(52) U.S. Cl.
CPC ...................... *A61B 6/035* (2013.01)

(58) Field of Classification Search
CPC ...................................................... A61B 6/035
USPC ........................ 378/4, 15, 19, 196, 197, 198
See application file for complete search history.

(56) References Cited

U.S. PATENT DOCUMENTS

| | | | |
|---|---|---|---|
| 6,510,195 B1 | 1/2003 | Chappo et al. | |
| 7,438,471 B2 | 10/2008 | Tybinkowski et al. | |
| 7,582,879 B2 | 9/2009 | Abenaim et al. | |
| 2002/0064252 A1* | 5/2002 | Igarashi et al. | 378/4 |
| 2004/0017895 A1* | 1/2004 | Suzuki et al. | 378/146 |
| 2007/0053479 A1* | 3/2007 | Sadatomo et al. | 378/4 |
| 2007/0053483 A1* | 3/2007 | Nagata et al. | 378/8 |
| 2008/0165921 A1* | 7/2008 | Tkaczyk et al. | 378/19 |
| 2013/0077737 A1* | 3/2013 | Fasoli | 378/4 |

OTHER PUBLICATIONS

Non-Final Office Action cited in U.S. Appl. No. 13/440,268 dated Nov. 25, 2013, 14 pgs.
Reply Non-Final Office Action cited in U.S. Appl. No. 13/440,268 dated Feb. 25, 2014, 11 pgs.
Notice of Allowance cited in U.S. Appl. No. 13/440,268 dated May 5, 2014, 14 pgs.

* cited by examiner

*Primary Examiner* — Glen Kao
(74) *Attorney, Agent, or Firm* — Cooper Legal Group LLC

(57) ABSTRACT

Among other things, a rotatable drum for a radiology imaging modality is provided herein. The rotatable drum comprises a bore, defined by an inner circumference of a sidewall of the rotatable drum. In one embodiment, the sidewall comprises one or more apertures through which radiation may pass. By way of example, a radiation source and a detector array may be mounted outside of the bore (e.g., on an outside surface of the sidewall) and apertures in the sidewall may permit radiation to pass from the radiation source to the detector array without being attenuated by the sidewall of the drum. In another embodiment, the detector array may be comprised of a plurality of detector modules that may be individually mounted/dismounted from the rotatable drum, and in one example, may provide structural support to the rotatable drum.

20 Claims, 7 Drawing Sheets

ROTATABLE DRUM ASSEMBLY FOR RADIOLOGY IMAGING MODALITIES

BACKGROUND

The present application relates to a rotatable drum for radiology imaging modalities (e.g., imaging modalities that utilize radiation to examine an object). It finds particular application in the field of computed tomography (CT) imaging utilized in medical, security, and/or industrial applications, for example. However, it also relates to other radiology modalities where at least one of a radiation source and/or a detector array is rotated about an object under examination.

Today, CT and other radiology imaging modalities (e.g., mammography, digital radiography, single-photon emission computed tomography, etc.) are useful to provide information, or images, of interior aspects of an object under examination. Generally, the object is exposed to radiation (e.g., X-rays, gamma rays, etc.), and an image(s) is formed based upon the radiation absorbed and/or attenuated by the interior aspects of the object, or rather an amount of radiation photons that is able to pass through the object. Typically, highly dense aspects of the object (or aspects of the object having a composition comprised of higher atomic number elements in the case of duel-energy) absorb and/or attenuate more radiation than less dense aspects, and thus an aspect having a higher density (and/or high atomic number elements), such as a bone or metal, for example, will be apparent when surrounded by less dense aspects, such as muscle or clothing.

Radiology imaging modalities generally comprise, among other things, one or more radiation sources (e.g., an X-ray source, Gamma-ray source, etc.) and a detector array comprised of a plurality of pixels that are respectively configured to convert radiation that has traversed the object into signals that may be processed to produce the image(s). As an object is passed between the radiation source(s) and the detector array, radiation is absorbed/attenuated by the object, causing changes in the amount/energy of detected radiation.

In some applications, such as in security and/or industrial applications, there is a trend toward high throughput imaging. For example, a baggage inspection apparatus at an airport may be designed to image 1000 or more bags per hour (e.g., although some inspection apparatuses may be designed for to handle less bags per hour). In such applications, the radiology imaging modality is typically configured to acquire information (e.g., X-ray information) sufficient to produce the image(s) while the object under examination is being continuously translated through the examination region.

There is also a trend in some applications, such as in security and/or industrial applications, for volume imaging, where a three-dimensional (3D) image of the object is generated. It will be appreciated that a 3D image typically provides substantially more detail about the object under examination than a two-dimensional (2D) image, which may improve automatic and/or manual threat detection, for example. To generate such a 3D image, the object is typically divided into a plurality of slices and each slice is viewed from a plurality of angles, typically by rotating the radiation source(s) and/or detector array about the object as it is being examined. For example, the radiation source and/or detector array may be mounted to a rotating gantry, such as a rotating disk, for example, and the rotating gantry may be configured to rotate about the object under examination. Traditionally, the detector array and/or radiation source have been cantilevered to the rotating gantry (e.g., requiring substantial forces to be counterbalanced or otherwise accounted for).

To generate a volumetric image of an object in a high throughput environment, a large number of slices of the object are typically acquired concurrently while the rotating gantry is rotating at a relatively high speed. Therefore, the detector array must be large enough to accommodate examining numerous slices of the object concurrently. Such a detector array may be referred to as a wide-area detector array because of its large surface area in the x- and/or z-directions. The size and/or weight of such a detector poses some challenges to the traditional cantilevered design. For example, when the detector is rotating at a high speed (e.g., 150 ms per rotation), the forces of a wide-area detector array may be substantial.

SUMMARY

Aspects of the present application address the above matters, and others. According to one aspect a computed tomography (CT) imaging modality is provided. The imaging modality comprises an X-ray source configured to emit X-ray radiation towards an object under examination and an X-ray detector array configured to detect at least a portion of the emitted X-ray radiation that traversed the object under examination. The imaging modality also comprises a rotatable drum assembly comprising a bore wherein the object is positioned during an examination. The rotatable drum is configured for rotation about the object. The X-ray source and X-ray detector array mounted substantially diametrically opposite one another on the rotatable drum and the rotatable drum comprises a first aperture within a sidewall of the rotatable drum through which X-ray radiation is configured to pass.

According to another aspect, a radiology imaging modality is provided. The imaging modality comprises a radiation source configured to emit radiation towards an object under examination and a detector array configured to detect at least a portion of the emitted radiation. The imaging modality also comprises a rotatable drum assembly comprising a bore wherein the object is positioned during an examination. The radiation source and the detector array are mounted substantially diametrically opposite one another on the rotatable drum. A sidewall of the rotatable drum comprises an interior surface defining a circumference of the bore, and at least one of the radiation source and the detector array are positioned outside of the bore. The imaging modality further comprises a support frame for supporting the rotatable drum.

According to another aspect, a computed tomography (CT) imaging modality is provided. The imaging modality comprises a support frame and an X-ray source configured to emit X-ray radiation towards an object under examination. The imaging modality also comprises an X-ray detector array configured to detect at least a portion of the emitted X-ray radiation that traversed the object under examination. The imaging modality further comprises a rotatable drum assembly comprising a bore wherein the object is positioned during an examination. The rotatable drum is configured for rotation about the object. The X-ray source and the X-ray detector array are mounted substantially diametrically opposite one another on the rotatable drum, and the rotatable drum comprises a first aperture within a sidewall of the rotatable drum through which the emitted X-ray radiation is passed. The imaging modality also comprises a bearing configured to rotate the rotatable drum relative to the support frame during the examination of the object.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
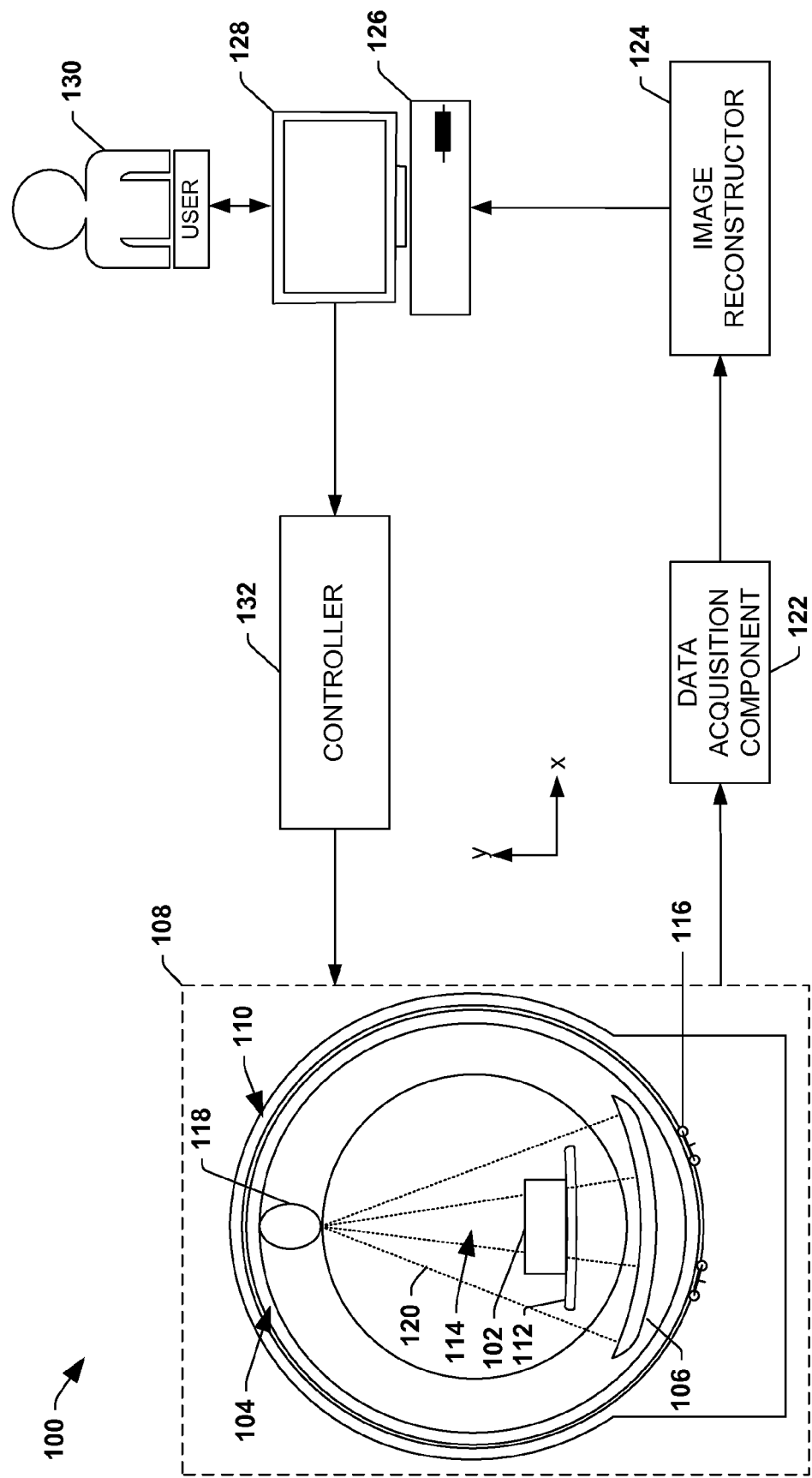
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, a rotatable drum (e.g., also referred to herein as a rotating gantry) for supporting a detector array and/or a radiation source of a radiology imaging modality is provided herein. A detector array may be supported in an aperture of the rotatable drum and may, in one embodiment, provide structural support for the drum. In this way, the detector array may be supported on both sides of the rotatable drum (e.g., as opposed to being cantilevered from a disk as described above). Moreover, in one embodiment, the detector array may be comprised of a plurality of (interchangeable) modules that can be configured to be individually mounted and/or dismounted from the rotating gantry. In this way, if a portion of a module should function improperly, merely the improperly functioning module may be dismounted from the rotating gantry and/or replaced. These and other features may be realized from the following disclosure.

FIG. 1 is an illustration of an example environment 100 comprising an example radiology or radiation imaging modality that may be configured to generate data (e.g., images) representative of an object 102 or aspect(s) thereof under examination. It will be appreciated that the features described herein may find applicability to other imaging modalities besides the example computed tomography (CT) scanner illustrated in FIG. 1. For example, the rotatable drum 104 described herein may find applicability to other types of radiology imaging modalities, such SPECT modalities. Moreover, the arrangement of components and/or the types of components included in the example environment 100 are for illustrative purposes only. For example, the rotatable drum 104 (also referred to herein as a rotating gantry) may be comprised of additional components to support the operation of a radiation source 118 and/or detector array 106 (e.g., such as a cooling unit). As another example, at least a portion of a data acquisition component 122 may be comprised within and/or attached to the detector array 106.

In the example environment 100, an examination unit 108 of the imaging modality is configured to examine one or more objects 102. The examination unit 108 can comprise a rotatable drum 104 and a (stationary) support structure 110, also referred to herein as a frame, which may encase and/or surround as least a portion of the rotatable drum 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotatable drum 104), and the rotatable drum 104 can be rotated and/or supported about the object(s) 102 by a rotator 116, such as a bearing, motor, belt drive unit, drive shaft, chain, roller truck, etc.

The rotatable drum 104 may surround a portion of the examination region 114 and may comprise one or more radiation sources 118 (e.g., an ionizing X-ray source, gamma radiation source, etc.) and a detector array 106 that is mounted on a substantially diametrically opposite side of the rotatable drum 104 relative to the radiation source(s) 118.

During an examination of the object(s) 102, the radiation source(s) 118 emits fan, cone, wedge, and/or other shaped radiation 120 configurations from a focal spot(s) of the radiation source(s) 118 (e.g., a point within the radiation source(s) 118 from which radiation 120 emanates) into the examination region 114. It will be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 can comprise a linear (e.g., one-dimensional) or two-dimensional array of elements disposed as a single row or multiple rows in the shape of a square, rectangle, and/or spherical arc, for example, typically having a center of curvature at the focal spot of the radiation source(s) 118, for example. As the rotating gantry 104 rotates, the detector array 106 is configured to directly convert (e.g., using amorphous selenium and/or other direct conversion materials) and/or indirectly convert (e.g., using Cesium Iodide (CsI) and/or other indirect conversion materials) detected radiation into electrical signals.

Signals that are produced by the detector array 106 may be transmitted to a data acquisition component 122 that is in operable communication with the detector array 106. Typically, the data acquisition component 122 is configured to convert the electrical signals output by the detector array 106 into digital data and/or to combine the digital data acquired during a measuring interval. The collection of digital output signals for a measuring interval may be referred to as a "projection" or a "view". Moreover, an angular orientation of the rotating gantry 104 (e.g., and the corresponding angular orientations of the radiation source(s) 118 and the detector array 106) relative to the object(s) 102 and/or support article 112, for example, during generation of a projection may be referred to as the "projection angle."

The example environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed of gantry rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

It will be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components to perform additional features, functions, etc. (e.g., such as automatic threat detection).

Figure 2:
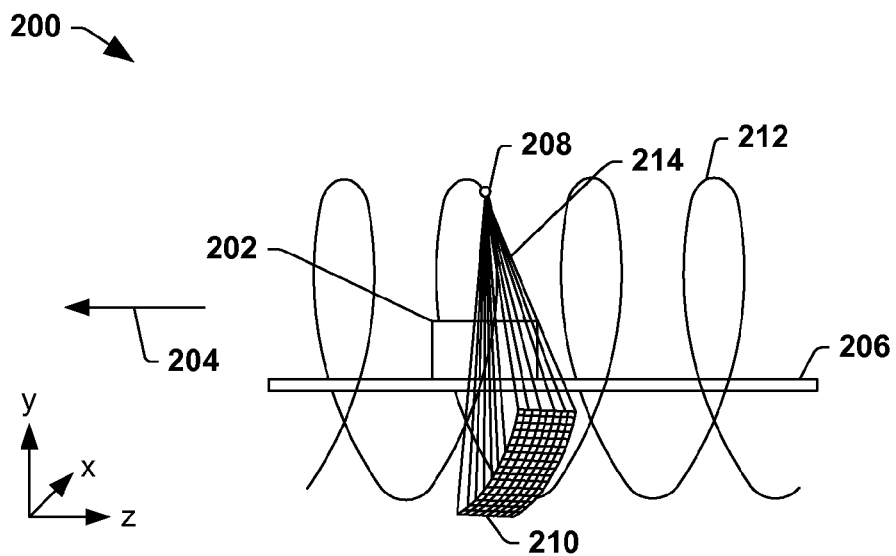
FIG. 2 illustrates a functional diagram of a helical CT imaging modality.

FIG. 2 is a functional diagram 200 of a helical radiology imaging modality. In such an imaging modality, an object 202 (e.g., 102 in FIG. 1) under examination is translated 204 (typically at a constant speed) along a z-axis (e.g., parallel to an axis of rotation) via an object support 206 (e.g., 112 in FIG. 1). Typically, while the object 202 is being translated, one or more radiation sources 208 (e.g., 118 in FIG. 1) and/or a detector array 210 (e.g., 106 in FIG. 1) are rotated about the object 202 (in an x and/or y direction) via a rotatable drum (e.g., 104 in FIG. 1), causing the radiation source(s) 208 and/or the detector array 210 to follow a spiral or helical-like trajectory 212 relative to the object (e.g., where the source 208 and detector array 210 do not move in the z direction, and thus the helical trajectory is established by the combination of the x/y rotation of the source 208 and detector array 210 and the z-axis translation of the object 202). As the object 202 is translated, data for a prescribed number of slices of the object 202 is acquired via detected radiation 214. For example, in one embodiment, 16 or more slices of the object 202 may be acquired concurrently via the detector array 210. It will be appreciated that the z-axis indicates the axial direction along which slices of the object 202 are taken, while the x-axis is one of the coordinates of a plane within which a tile of the detector array 210 may be disposed.

Figure 3:
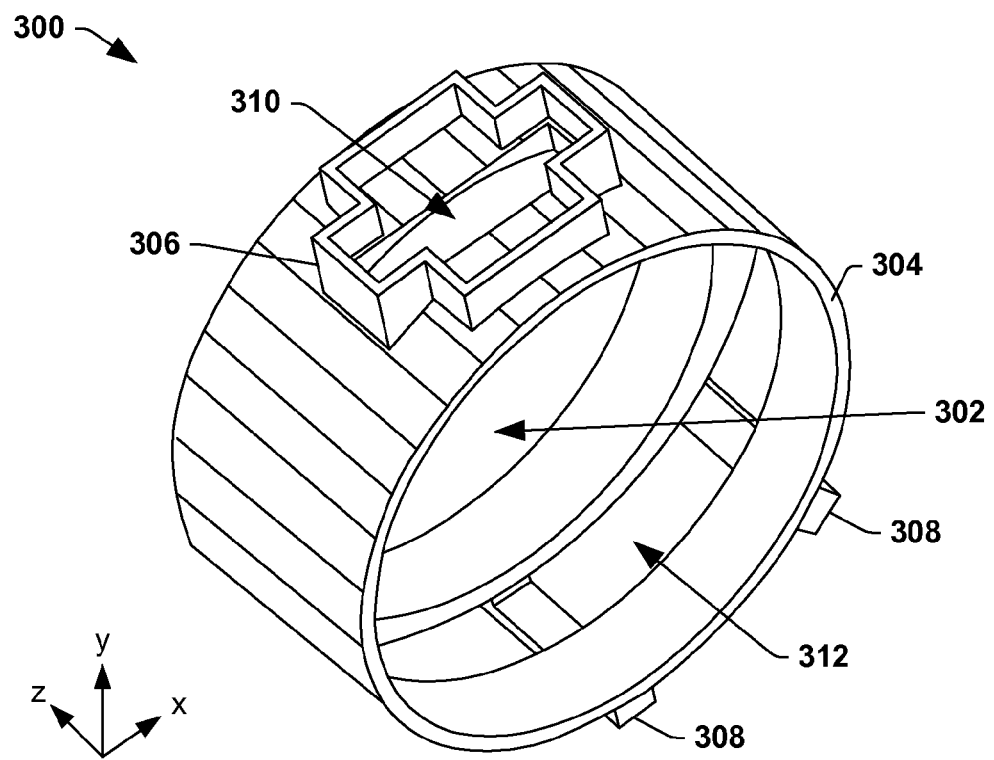
FIG. 3 illustrates an example rotatable drum comprising apertures through which radiation may pass.

FIG. 3 illustrates an example rotatable drum 300 (e.g., 104 in FIG. 1) configured for rotation about an object under examination. Although not illustrated, a radiation source and/or a detector array may be mounted to the drum 300. In this way, as the drum 300 rotates, the radiation source and/or detector array may also be rotated, causing an object under examination to be viewed from a plurality of angles to generate volumetric data, for example.

The rotatable drum 300 is typically defined by a circular cylinder geometry (e.g., or a right circular cylinder) having a bore 302 wherein an object may be positioned during an examination. By way of example, the drum 300 may have diameter of 4 to 5 feet, with merely 2-3 inches of the diameter being occupied by a sidewall 304 of the drum 300. Thus, the bore 302 may have a diameter that is just a few inches smaller than the diameter of the drum 300. Stated another way, the drum may have an inner diameter, which corresponds to the diameter of the bore, and an outer diameter, which may generally be regarded as the diameter of the drum. It may be appreciated that, unless otherwise noted, dimensions stated herein, including absolute and/or relative dimensions (e.g., such as dimensions of the bore 302 relative the drum 300) are merely intended to be example dimensions, and the instant disclosure is not intended to be limited to such dimensions.

As used herein, "circular cylinder" is intended to be used in an ordinary sense, where an inner circumference, defined by an interior surface of the sidewall 304, and/or an exterior circumference, defined by an exterior surface of the sidewall 304, is substantially circular in shape. However, other geometries, such as elliptic cylinders, are also contemplated for the drum 300. It may be appreciated, however, that although the drum 300 may be designed to comprise a circular or elliptical geometry, defects in the machining and/or manufacturing of the drum 300 may cause the rotatable drum 300 to deviate from a perfectly circular or perfectly elliptic cylinder, for example. Thus, the drum may not comprise a perfectly circular or elliptical shape.

Further, while the drum 300 may be referred to as circular and/or elliptical some aspects of the drum 300 may deviate from the overall circular/elliptical geometry. For example, the drum 300 may be machined and/or manufactured to accommodate and/or receive one or more components that are configured to be selectively coupled to the rotating drum 300. By way of example, in the illustrated embodiment, the rotatable drum 300 comprises a protruding member 306 extending from the exterior surface of the sidewall 304 (e.g., a diametrically opposite surface of the sidewall relative to the interior surface) into which a portion of a radiation source may be seated (e.g., to secure the radiation source to the rotating drum 300 and/or to mitigate movement/vibration of the source during rotation of the drum 300). The example rotatable drum 300 further comprises one or more support bars 308 (e.g., extending from the exterior surface of the sidewall 304) to provide structural support and/or rigidity to the rotatable drum 300 when an aperture 312 (e.g., a window or opening), divides a portion of the sidewall 304 to accommodate a detector array (e.g., which may be positioned substantially flush with the sidewall 300 (e.g., such that a surface of the detector array is flush with an interior surface of the sidewall 304)). It will be appreciated that these features and/or other features of the rotatable drum 300 that are described herein are merely example features unless otherwise noted and are not intended to limit the scope of the claims to the extent practical. For example, in another embodiment, the drum 300 may not comprise the support bars 308 and/or the protruding member 306 illustrated herein. Moreover, in another embodiment, the drum 300 may be machined and/or manufactured with weights to weight a first aspect of the drum 300 differently than another aspect of the drum 300 (e.g., to facilitate balance or somewhat even weight distribution when the radiation source, detector array, and/or other components are applied to the drum).

As will be described in more detail below, in one embodiment, the radiation source and/or the detector array are mounted outside of the bore 302, which may be defined by the interior surface of the sidewall 304 (e.g., the circumference of the bore may be defined by interior surface of the sidewall). Thus, the sidewall 304 of the drum 300 may comprise one or more apertures, or windows, to accommodate the position of the radiation source and/or detector array (e.g., and/or other components). More specifically, depending upon the composition of the rotatable drum, radiation may be attenuated by the drum 300 if the radiation passes through the sidewall 304. Thus, the drum 300 may comprise a first aperture 310 (e.g., window) in the sidewall 304 through which radiation, emitted from the radiation source, may pass to enter the bore 302. Further, the sidewall 304 may comprise a second aperture 312 into which the detector array may be positioned and/or through which radiation may pass to impinge the detector array with little to no attenuation by the sidewall 304, for example. Other apertures may also (or alternatively) exist to accommodate other components, such as electronic components mounted to the drum 300, for example.

It will be appreciated that the need for apertures to accommodate the movement of radiation may depend upon, among other things, the location of the radiation source, the location of the detector array, and/or the composition of the drum 300 (or more particularly the sidewall 304). For example, in another embodiment (not shown), the radiation source and/or the detector array may be positioned within the bore 302. When both the radiation source and the detector array are positioned within the bore 302, the apertures 310, 312 described above (e.g., for permitting radiation to pass through the sidewall 304) may be unnecessary. Moreover, where the composition of the drum 300 comprises a radiation transparent material (e.g., a material that attenuates little if any radiation, such as some plastics), the apertures 310, 312, may be unnecessary regardless of whether the radiation source and/or detector array are mounted within and/or outside of the bore 302. Conversely, if the drum 300 is comprised of a radiation opaque material, such as a metal material, for example, one or more apertures for radiation passage may be desirable to mitigate attenuation by the sidewall 304 if the radiation source and/or the detector array are mounted outside of the bore 302, for example.

The construction of the rotatable drum 300 may be a function of, among other things, the composition of the drum 300 and/or the desire for the drum 300 to have a smooth surface(s). More specifically, the drum 300 may be formed with a uni-body construction or may be formed from two or more segments that are fastened/secured together. As an example, in one embodiment, the rotatable drum is formed with uni-body construction machined/lathed from a block of metal. In another embodiment, the rotatable drum 300 is comprised of a plurality of metal and/or plastic (and/or other material(s)) segments that are bolted, welded, soldered, or otherwise brought together to form the drum 300, for example.

Figure 4:
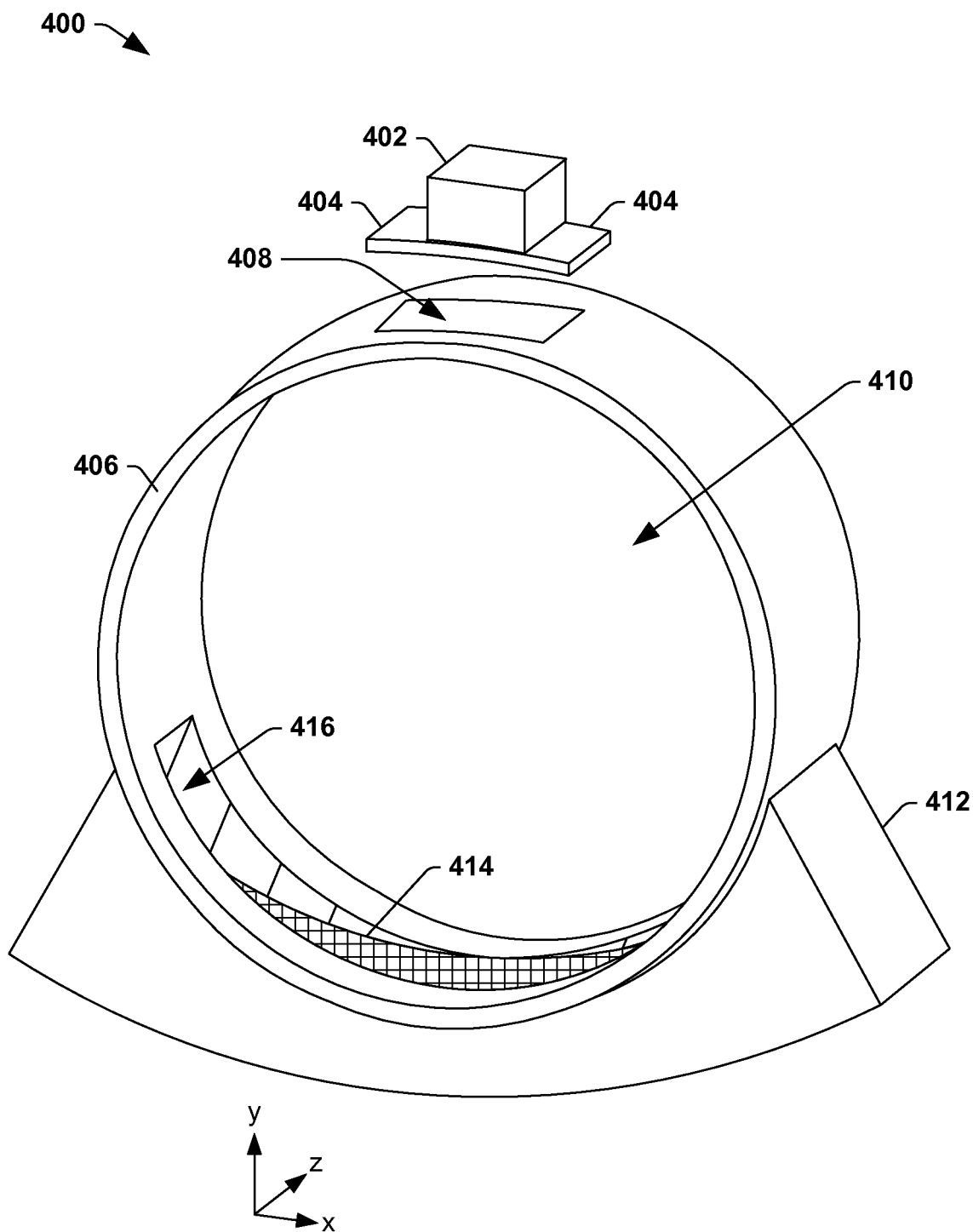
FIG. 4 illustrates an example rotatable drum comprising a top mounted radiation source and a channel into which a detector array may be positioned.

FIG. 4 illustrates another embodiment of an example drum 400 (e.g., 104 in FIG. 1) configured for rotation about an object under examination. In this embodiment of the example drum 400, a radiation source 402 (e.g., 118 in FIG. 1) comprises one or more flanges 404 for securing the radiation source 402 to the rotatable drum 404 and the example drum 400 does not comprising a protruding member (e.g., 306 in FIG. 3). For example, the radiation source 402 may be mounted to an external surface of a sidewall 406 (e.g., 304 in FIG. 3), and the sidewall 406 may comprise an aperture 408 (e.g., 310 in FIG. 1) through which radiation is transmitted from the radiation source 402 to a bore 410 (e.g., 302 in FIG. 3) in which an object under examination may be positioned. In another embodiment, the radiation source 402 may be mounted, via the flanges 404, on an underside of the aperture 408 (e.g., on an inner surface of the sidewall 406), and the radiation source 402 may protrude through the aperture 408, for example. In another example, a combination of sorts may exist where the radiation source has one or more flanges and the drum comprises one or more protrusions to facilitate mounting the radiation source to the drum. It may be appreciated that the same holds true for other components (e.g., detector array and/or components, modules, etc. thereof) where a combination of one or more protrusions, flanges, etc. may be used to facilitate mounting, coupling, seating, etc.

Moreover, as opposed to (or in combination with) one or more support bars (308 in FIG. 3) being attached to the rotatable drum 400, the drum 400 may comprise a structure 412 that protrudes from the rotatable drum 400 and creates a channel 416, for example, into which a detector array 414 (e.g., 106 in FIG. 1) (e.g., represented by the square pattern) may be positioned/seated. In this way, the underside of the detector array 414 may rest on the substantially solid structure 412, for example, to mitigate movement of the detector array 414 while the drum 400 is rotating, for example. Moreover, such a structure 412 may provide additional structural support to the drum 400 than (merely) the support bars 308 described with respect to FIG. 3, for example.

In yet another embodiment, the detector array 414 may be positioned within the bore itself, and thus the structure 412 protruding from the rotatable drum 400 (and/or support bars) may be unnecessary (e.g., the detector array may merely rest on an inner surface of the sidewall 406, for example.

Figure 5:
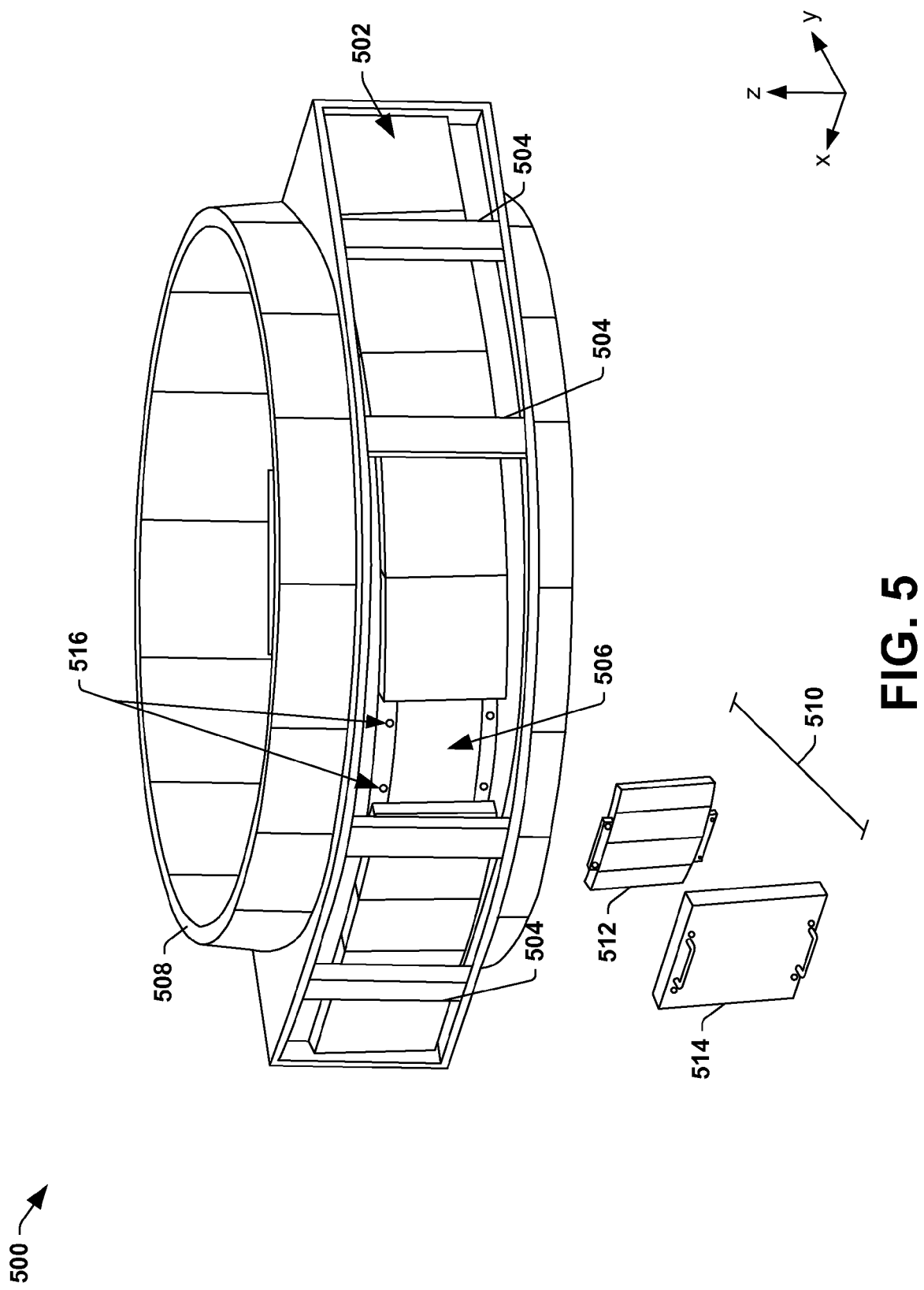
FIG. 5 illustrates a bottom-up view of a rotatable drum to which detector modules of a detector array may be mounted.

FIG. 5 illustrates a bottom-up view of a rotatable drum 500 (e.g., 300 in FIG. 3) illustrating an underside of a detector array 502 (e.g., 106 in FIG. 1) and support bars 504 (e.g., 308 in FIG. 3) that may span an aperture 506 (e.g., 312 in FIG. 3) of the drum 500. It will be appreciated that for purposes of describing the drum, 500, a portion of the detector array 502 (e.g., a selective removable module) has been removed to illustrate the aperture 506 in the sidewall 508 of the drum 500. It may be appreciated that during an operation of the drum 500 (e.g., an examination of an object), it may be preferable that apertures of the drum 500 be closed via the detector array 502 and/or a radiation source, for example. That is, the detector array 502 and/or radiation source may be positioned to cover (at least some) apertures in the drum 500, for example.

As briefly discussed above and as will be described in more detail with respect to FIGS. 6-7, in one embodiment, the detector array 502 may be comprised of a plurality of modules that together comprise the assembled detector array 502. For example, in the illustrated embodiment, one module 510 of the plurality of modules has been removed to illustrate how the modules may be individually coupled and/or uncoupled from the drum 500. That is, in one embodiment, respective modules may be mounted to the drum 500 independently of other modules of the detector array 502. As an example, in the illustrated embodiment, the drum 500 may comprise a machined mounting surface comprises screw holes 516 (and/or other types of apertures that facilitate mounting, fastening, etc.) and the module 510 may be coupled to the drum 500 through one or more screws, bolts, etc. that pass through corresponding apertures in the module 510 and get secured into the drum 500 via 516, for example. Other techniques for fastening, securing, etc. a module 510 to the drum 500 are also contemplated (e.g., adhesive(s), friction fit, etc.). In one embodiment, the drum 500 and/or detector module 510 may also comprise alignment pins to provide alignment of the module 510 with the drum 500, for example.

Respectively modules may be comprised of, among other things, an anti-scatter grid 512 and a detector assembly 514. The anti-scatter grid 512 is configured to reduce an amount of secondary radiation that impinges the detector array. The detector assembly 514, which may comprise a detector sub-assembly and an electronics sub-assembly, is configured to convert radiation into data that may be used to generate an image of an object under examination. In this way, a single module 510 may be considered a miniature detector measurement system (DMS) and a plurality of modules 510 may be combined to form the detector array (e.g., such as a wide-area detector array).

It will be appreciated that there are numerous advantages to the modular assembly of the detector array 502 over traditional, non-modular detector arrays. For example, when a portion of a module 510 malfunctions, merely the module, or a portion thereof, may be replaced as opposed to replacing the entire detector array 502. Moreover, in one embodiment, the modules 510 may be interchangeable. Thus, when a portion of a module 510 malfunctions, the malfunctioning module can be replaced with another module while the module is being repaired to reduce downtime of the radiology imaging apparatus, for example.

Figure 6:
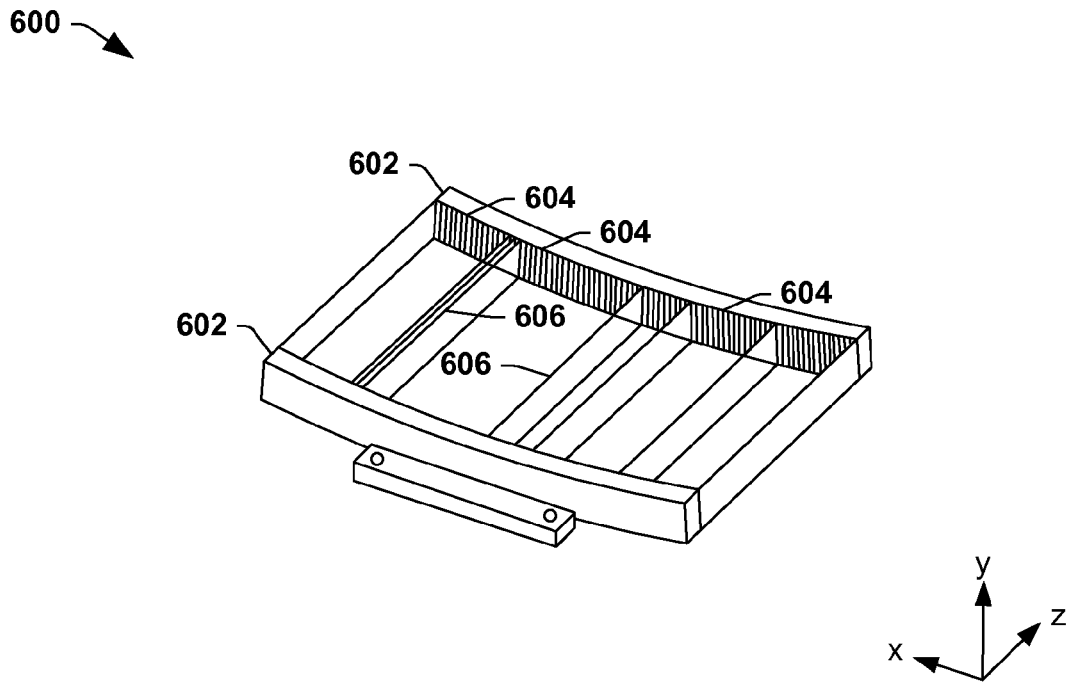
FIG. 6 illustrates an example anti-scatter grid of an example detector module.

FIG. 6 illustrates an example anti-scatter grid 600 (e.g., 512 in FIG. 5) of a detector module (e.g., 510 in FIG. 5) configured to reduce an amount of secondary radiation that impinges an underlying detector. It may be appreciated that secondary radiation is used herein to refer to radiation that has been deflected after having been emitted by radiation source. That is, the radiation does not follow a straight path from the source to the detector array. Conversely, primary radiation (e.g., which is desirable) typically follows a straight path from the radiation source to the detector array.

The anti-scatter grid 600 comprises one or more mounting brackets 602 which are used to attach the anti-scatter grid 600 to a rotatable drum (e.g., 500 in FIG. 1). Within the mounting brackets 602 may be comprised slits 604 that are cut or other inscribed, for example, into the mounting bracket 602, and which may act as guides for respective anti-scatter plates 606. For example, in the illustrated embodiment, the slits on an interior wall of the mounting brackets 602 may be configured to receive anti-scatter plates 606. It will be appreciated that for ease of understanding the configuration of the anti-scatter grid 600, the grid 600 is illustrated as merely comprising several anti-scatter plates 606. However, in practice, most, if not all, of the slits may be comprised of an anti-scatter plate 606, for example.

The anti-scatter plates 606 are comprised of a radiation absorbing material. For example, in one embodiment, respective plates 606 are comprised of tungsten that is bonded to the slit 604 via an epoxy, for example. However, other materials may be used for the anti-scatter plates 606 and/or to affix the plates 606 to the mounting brackets 602, for example. Further, it one embodiment, one or more anti-scatter plates 606 of the grid 600 may be flared. For example, a top surface of a plate, facing the radiation source (e.g., coming out of the page), may comprise a thickness of about 0.01 inches and a bottom surface of the plate, facing the detector array (e.g., going into the page), may comprise a thickness of about 0.02 inches. In this way the flared plates may essentially comprise a triangular cross-section, for example.

Figure 7:
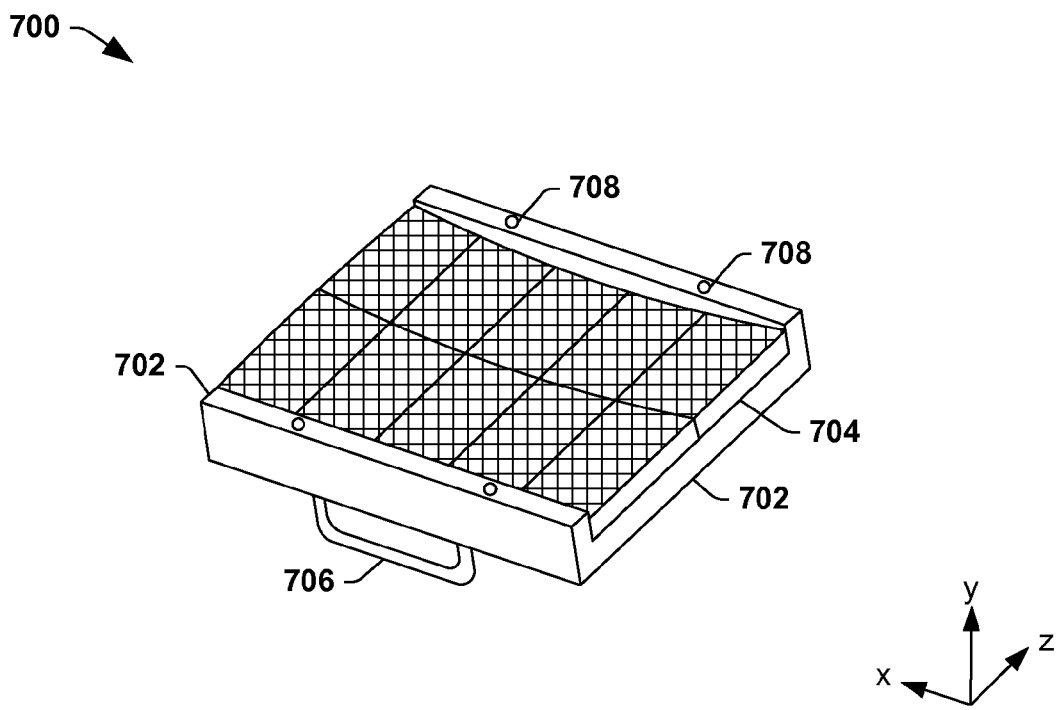
FIG. 7 illustrates an example detection assembly of an example detector module.

FIG. 7 illustrates an example detection assembly 700 (e.g., 514 in FIG. 5) of a detector module (e.g., 510 in FIG. 5) configured to be mounted to a rotatable drum (e.g., 500 in FIG. 5). The assembly 700 comprises a mounting bracket 702, a detection unit 704, and a handle(s) 706 for gripping the detection assembly 700 (e.g., as it is mounted to and/or dismounted from the drum), for example.

In one embodiment, such as where the rotatable drum comprises as aperture wherein the assembly 700 is mounted (e.g., as illustrated in FIGS. 3 and 5), the mounting bracket 702 of the assembly 700 may be configured to provide structural support to the rotatable drum (e.g., in addition to and/or in substitution for one or more support brackets, bars, etc.). Thus, as illustrated, the mounting bracket 702 may be configured to extend across a detection unit 704, or across an underside of the detection unit 704, and may comprise one or more mounting holes 708 configured for mounting the assembly 700 to the rotatable drum. Moreover, the mounting bracket 702 may be comprised of a material that can provide structural support, such as steel, and/or may be of a sufficient thickness to support the rotatable drum (e.g., to keep the drum from separating, flexing, etc. proximate an area of the drum where the detector array is positioned).

In another embodiment, such as where a solid structure extends underneath the detector array as illustrated in FIG. 4, the mounting brackets 702 may merely be configured to provide rigidity to the assembly 700. Thus, the mounting brackets 702 may be comprised of a lighter weight material and/or may be thinner than the mounting brackets described above that may be configured to provide at least partial structurally support to the drum.

In one embodiment, respective detector assemblies 700 may be configured as a complete digital acquisition component (e.g., 122 in FIG. 1) or digital measurement system. That is, respective assemblies 700 may be configured to detect radiation that impinges thereon, convert the radiation to electrical signals, and convert the electrical signals to digital data, which can be combined with digital data produced by other modules to form an image, for example. In such an embodiment, respective assemblies 700 may comprise a detector sub-assembly (e.g., comprised of one or more detectors) configured to convert detected radiation into electrical signals and an electronic subassembly configured to convert the electrical signals into digital data. One such example arrangement is described in U.S. application Ser. No. 13/440,268 assigned to Analogic Corporation, entitled "TILE FOR DETECTOR ARRAY OF IMAGING MODALITY HAVING SELECTIVELY REMOVABLE/REPLACEABLE TILE SUB-ASSEMBLIES" at least some of which is incorporated herein by reference. As described therein, an assembly 700 comprises a plurality of tiles, with respective tiles comprising a detector sub-assembly and an electronics sub-assembly. However, other arrangements are also contemplated. For example, in another embodiment, the assembly 700 may comprise a plurality of detector sub-assemblies and merely one electronic sub-assembly, for example. Moreover, in another embodiment, respective assemblies 700 may merely comprise a detection portion, for example, the conversion of electrical signals to digital data may be performed by a data acquisition component shared by a plurality of modules, for example.

Figure 8:
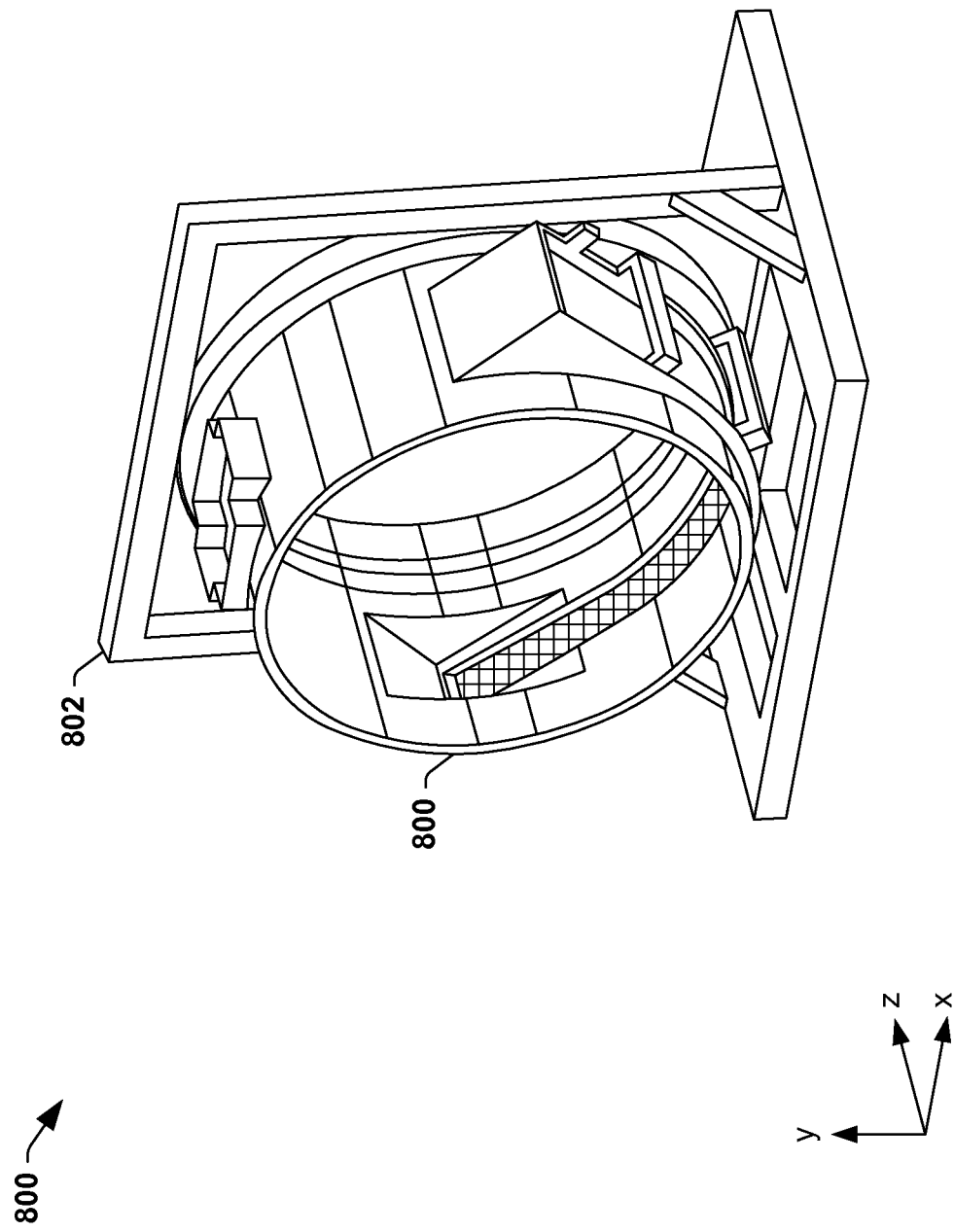
FIG. 8 illustrates an example rotatable drum positioned within a support frame for support the rotatable drum.

FIG. 8 illustrates an example rotatable drum 800 (e.g., 300 in FIG. 3) positioned within a support frame 802 (e.g., 110 in FIG. 1). As will be described in more detail below, the support frame 802 is configured to support the drum 800 and typically remains substantially stationary while the drum 800 rotates about the object under examination. For example, in one embodiment, the frame 802 comprises a first face of a bearing and the drum 800 comprises a second face of a bearing. Together, these two faces may provide for the drum 800 being rotated relative to the support frame 802.

Figure 9:
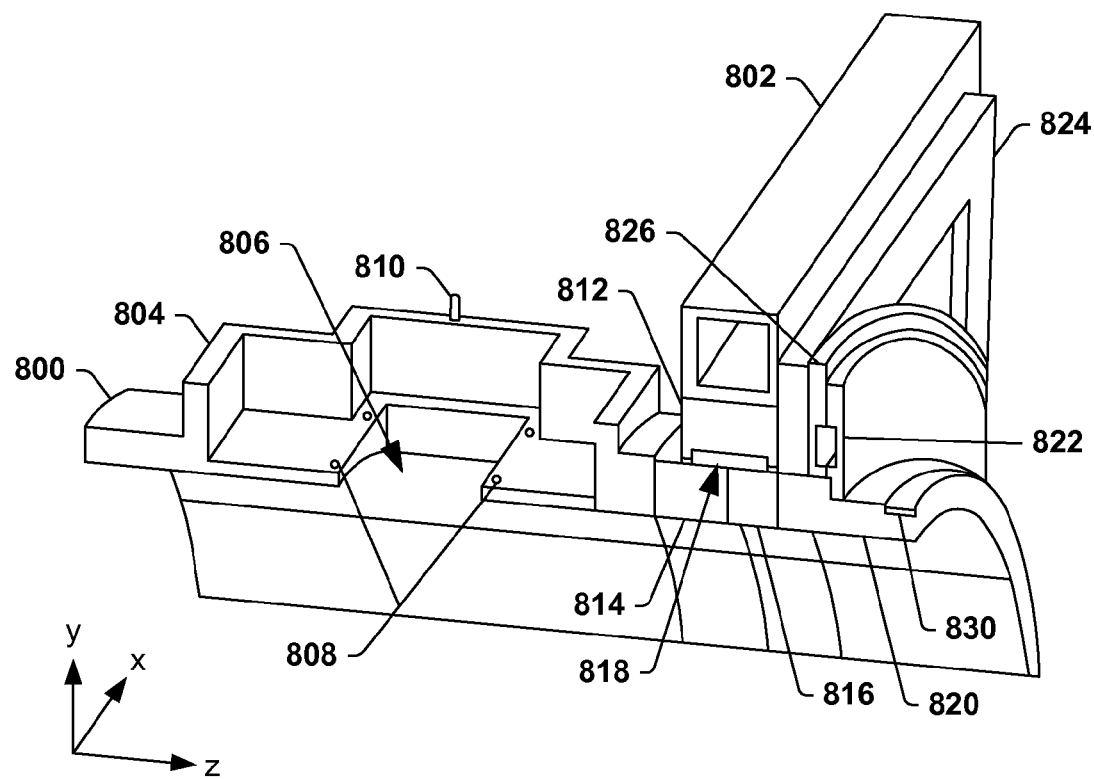
FIG. 9 illustrates a cross-sectional view of an example rotatable drum and support frame assembly.

FIG. 9 illustrates a cross-section of the rotatable drum 800 and support frame 802 comprising an example arrangement of components. Moving from left to right, the rotatable drum 800 comprises a protruding member 804 (e.g., 306 in FIG. 3) into which a portion of the radiation source (not shown) may be seated and an aperture 806 (e.g., 310 in FIG. 3) through which radiation emitted by the radiation source may pass to enter a bore of the drum 800, for example. It may be appreciated, the drum 800 may comprise one or more (machined) mounting surfaces for mounting the radiation source and/or a beam collimator that guides the radiation, for example. By way of example and not limitation, in the illustrated embodiment, the drum 800 comprises a plurality of screw holes 808 and an alignment pin 810 to facilitate mounting the radiation source and/or a beam collimator, for example, to the drum 800.

A bearing may be configured to physically couple the drum 800 to the support frame 802 and/or to provide for rotation of the drum 800. For example, in one embodiment, a first face 812 (e.g., an outer face) of the bearing may be coupled to the support frame 802, and a second face 814, 816 (e.g., an inner face) of the bearing may be coupled to the drum 800 (e.g., such that the drum 800 comprises the second face of the bearing). It will be appreciated that in the illustrated embodiment, the inner face is actually comprised for two face clamps 814 and 816 that may be physically coupled together to make up the second face, for example. However, in another embodiment, the first face 812 may be comprised of two or more face clamps while the second face 814, 816, coupled to the drum 800, may be merely comprised of a single face, for example. Between the first and second faces may be comprises a single or multi (e.g., dual) ball path 818, for example.

To extend the rotatable drum 800 and provide for coupling other components to the drum 800, a face extension 820 may be attached to the face clamp 816. The face extension 820 is configured to extend the drum 800 beyond the bearing, for example, to provide additional room for components on the rotational side of the imaging modality. For example, in one embodiment, a rotatable portion 822 of a power link, such as a slip-ring assembly and/or a contactless power link (e.g., as provided for in U.S. patent application Ser. No. 11/699,529, assigned to Analogic Corporation and at least partially incorporated herein by reference) may be coupled to the face extension 820 and may be configured to rotate as the drum 800 is being rotated. In other embodiments, a data link configured to provide for the transfer of image data and/or control data, for example, between the drum 800 and a stationary portion of the imaging modality may be affixed to the face extension 820, for example. Other embodiments may mount such components (and/or other components) to the drum 800 itself as opposed to a face extension 820, for example.

The support frame 802 may comprise opposing members of a power link and/or a data link. For example, in the illustrated embodiment, the support frame 802 comprises a mounting plate 824 and a stationary portion 826 of the power link, which may face the rotatable portion of 822 of the power link. The support frame 804 and/or mounting plate 824 (and/or other structures) may also comprise other components which may aid in the transfer of information and/or power between the drum 800 and stationary components of the imaging modality. For example, a stationary portion of a data link may be coupled to the mounting plate 824.

Figure 10:
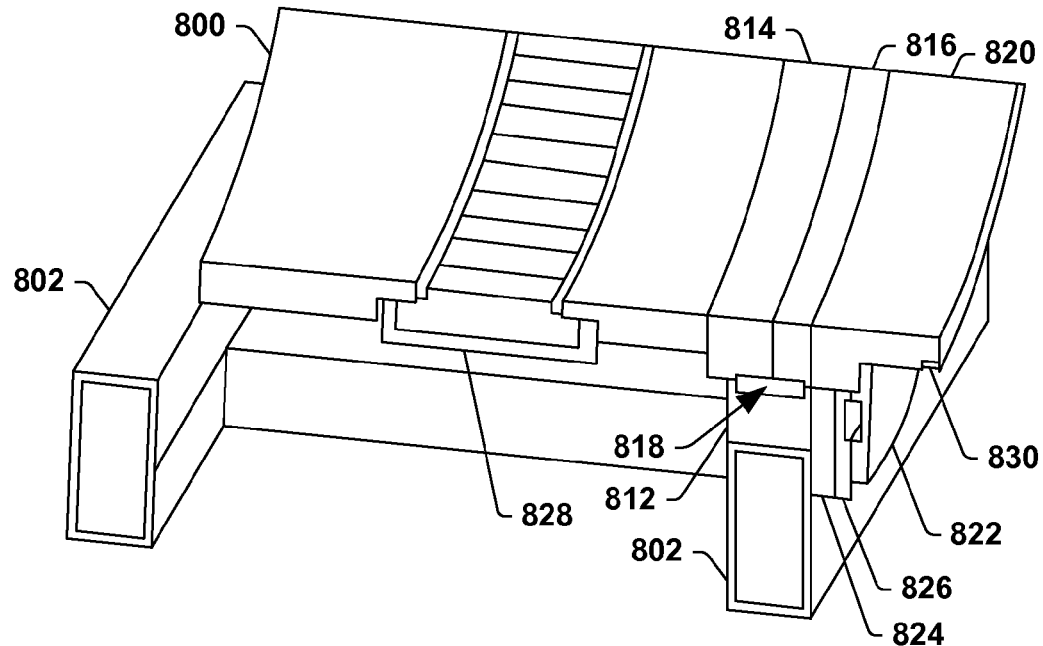
FIG. 10 illustrates a cross-sectional view of an example rotatable drum and support frame assembly.

FIG. 10 illustrates a second cross-section of the drum 800 and support frame 802 comprising an example arrangement of components. As illustrated, from this perspective, the drum 800 is essentially dissected into two portions separated by an aperture (e.g., 312 in FIG. 3) into which a detector array 828 (e.g., 502 in FIG. 5) (e.g., comprised of a plurality of detector modules (e.g., 510 in FIG. 5)) may be positioned. As described above, where the rotatable drum 800 is so dissected, the detector array 828 or modules thereof may comprise a mounting bracket that is configured to provide structural support to the drum 800 to reduce and/or mitigate flex of the drum 800, for example. Where, instead, the detector array 828 and/or modules of the detector array are seated in a channel of the rotatable drum 800 (e.g., as shown in FIG. 4 and not shown in FIG. 10), the drum itself may provide the structural support and thus little, if any, support may be provided by the detector array 828, for example.

As illustrated in FIG. 9, the second face of the bearing 814, 816 (e.g., the two inner face clamps) and the face extension 820 may be coupled to the rotatable drum. The rotatable portion 822 of the power link and/or other components may be coupled to the face extension 820. Further, a belt 830 may be seated in a channel of the face extension 820, for example, and connected to a belt drive unit (e.g., 116 in FIG. 1) to provide for rotating the face extension 820 and drum 800 relative to the support frame 802.

The first face 812 of the bearing and the mounting plate 824 (e.g., to which a stationary side 826 of the power link and/or data link may be coupled) are attached to the support frame 804.

It will be appreciated that the illustrated arrangement is merely intended to provide one example arrangement, and the instant application, including the scope of the claims, is not intended to be limited as such. By way of example, in another embodiment, the second face 814, 816 of the bearing may be attached to an outer surface of the drum 800 as opposed to a transverse surface as illustrated in FIGS. 9-10. In yet another embodiment, a bearing assembly may be attached to two or more (e.g., diametrically opposite) sides of the rotatable drum 800, as opposed to merely the single side illustrated in FIGS. 9-10. In this way, the weight of the load may be supported on a plurality of sides or faces, which may further stabilize the drum 800 and/or allow for utilization of certain types of bearings (e.g., bearings configured to support less than a cantilevered load), which may otherwise be excluded from use when the weight of the drum is supported by merely one bearing, for example.

Further, the placement of components in FIGS. 9-10 is merely intended to be illustrative. For example, the rotatable portion 822 of the power link may be positioned on the rotatable drum 800 and/or a rotatable portion of a data link may be positioned on the rotatable drum 800. Further, the belt 830 may be relocated to the drum 800 and/or a second belt may be physically coupled to the drum 800. Thus, there are numerous configurations for how components may be arranged, and the figures are merely intended to describe one example arrangement.

Moreover, while reference is made to a bearing assembling (e.g., such as a ball bearing, an air bearing, etc.) being used to couple the rotatable drum 800 to the frame 802, it may be appreciated that other techniques may exists for rotating an object relative to another object and/or supporting the rotatable object. By way of example, the frame may comprise a set of wheels, such as those described in U.S. Pat. No. 5,473,657 and/or PCT Application PCT/US2011/42567, assigned to Analogic Corporation and at least partially incorporated herein by reference, and the rotatable drum 800 may be seated/rested on the wheels. In such an embodiment, one or more of the wheels may act as a drive wheel, causing the drum 800 to rotate as an underlying wheel is rotated, for example. Thus, the wheels may support the weight of the load such that a bearing is not required for example. Alternatively, the drum/ frame assembly may comprise a bearing, but the rotation of the drum may be driven by a wheel and/or a belt, for example.

It may be appreciated that "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A computed tomography (CT) imaging modality, comprising:
    a rotatable drum assembly configured for rotation about an object and comprising:
        a drum defining a bore within which the object is positioned during an examination; and
        a structure that protrudes from the drum, the structure defining a channel within the rotatable drum assembly;
    an ionizing radiation source configured to emit ionizing radiation towards the object during the examination, the ionizing radiation source comprising at least one of an X-ray source or a gamma ray source; and
    a modular detector array assembly disposed within the channel and comprising:
        a first module configured to be mounted to a first portion of the rotatable drum assembly, comprising:
            a first anti-scatter module comprising a first plurality of anti-scatter plates; and
            a first detector module comprising a first plurality of pixels configured to convert a first portion of the ionizing radiation into first electrical signals; and
        a second module configured to be mounted to a second portion of the rotatable drum assembly, comprising:
            a second anti-scatter module comprising a second plurality of anti-scatter plates; and
            a second detector module comprising a second plurality of pixels configured to convert a second portion of the ionizing radiation into second electrical signals.

2. The imaging modality of claim 1, the first module in contact with the structure.

3. The imaging modality of claim 1, a sidewall of the drum defining a first aperture through which the ionizing radiation passes during the examination, the sidewall comprising an interior surface defining a circumference of the bore and an exterior surface on a diametrically opposite surface of the sidewall relative to the interior surface, the first module at least partially mounted to the exterior surface and at least partially covering the first aperture.

4. The imaging modality of claim 3, the ionizing radiation source at least partially mounted to the exterior surface.

5. The imaging modality of claim 1, a sidewall of the drum defining a first aperture and the first module configured to be mounted so as to be disposed within the first aperture.

6. The imaging modality of claim 1, the first detector module comprising a handle.

7. The imaging modality of claim 1, comprising a support frame configured to support the rotatable drum assembly during a rotation of the rotatable drum assembly.

8. The imaging modality of claim 7, comprising at least one bearing disposed between the support frame and the rotatable drum assembly, the at least one bearing configured to rotate the rotatable drum assembly relative to the support frame.

9. The imaging modality of claim 7, comprising a belt drive unit configured to rotate the rotatable drum assembly relative to the support frame.

10. The imaging modality of claim 1, the first module comprising a data acquisition system operably coupled to at least one of the first plurality of pixels.

11. The imaging modality of claim 10, the first module selectively detachable from the rotatable drum assembly.

12. The imaging modality of claim 1, the rotatable drum assembly formed with a uni-body construction.

13. The imaging modality of claim 1, the rotatable drum assembly comprising at least one of:
    a first machined mounting surface for mounting the ionizing radiation source to the rotatable drum assembly; or
    a second machined mounting surface for mounting at least one of the first module or the second module to the rotatable drum assembly.

14. An imaging modality for examining an object via ionizing radiation, comprising:
    an ionizing radiation source configured to emit ionizing radiation towards an object during an examination of the object, the ionizing radiation source comprising at least one of an X-ray source or a gamma ray source;
    a detector array configured to detect at least a portion of the ionizing radiation; and
    a rotatable drum assembly configured for rotation in a rotational plane about the object, the rotatable drum assembly comprising:
        a drum defining a bore within which the object is positioned during the examination; and a protruding member extending from a sidewall of the drum and comprising a first sidewall lying in a first plane parallel to the rotational plane and a second sidewall lying in a second plane parallel to the rotational plane, and the ionizing radiation source configured to be seated within the protruding member between the first sidewall and the second sidewall.

15. The imaging modality of claim 14, comprising a bearing disposed between the rotatable drum assembly and a support frame for supporting the rotatable drum assembly, the rotatable drum assembly physically coupled to a first face of the bearing and the support frame physically coupled to a second face of the bearing.

16. The imaging modality of claim 14, the detector array comprising a plurality of modules.

17. The imaging modality of claim 14, the sidewall of the drum defining an aperture and the detector array mounted so as to be positioned within the aperture.

18. The imaging modality of claim 14, the detector array configured to concurrently acquire 16 slices or more of the object.

19. The imaging modality of claim 14, the rotatable drum assembly comprising a weight to counterbalance a weight of at least one of the ionizing radiation source or the detector array.

20. A computed tomography (CT) imaging modality, comprising:
- a rotatable drum assembly configured for rotation about an object during an examination and comprising:
  - a drum defining a bore within which the object is positioned during the examination; and
  - a structure that protrudes from the drum and defines a channel;
- an ionizing radiation source mounted to the rotatable drum assembly and configured to emit ionizing radiation towards the object during the examination, the ionizing radiation source comprising at least one of an X-ray source or a gamma ray source;
- a detector array disposed within the channel and mounted to the rotatable drum assembly, the detector array configured to detect at least a portion of the ionizing radiation;
- a first anti-scatter module disposed within the channel and mounted to the rotatable drum assembly, the first anti-scatter module comprising a first plurality of anti-scatter plates; and
- a second anti-scatter module disposed within the channel and mounted to the rotatable drum assembly, the first anti-scatter module comprising a second plurality of anti-scatter plates.

\* \* \* \* \*